United States Patent
Taoka et al.

(10) Patent No.: US 8,265,226 B2
(45) Date of Patent: Sep. 11, 2012

(54) X-RAY IMAGE ACQUIRING APPARATUS

(75) Inventors: Akira Taoka, Hamamatsu (JP);
Kazuhisa Miyaguchi, Hamamatsu (JP)

(73) Assignee: Hamamatsu Photonics K.K.,
Hamamatsu-shi, Shizuoka (JP)

( * ) Notice: Subject to any disclaimer, the term of this patent is extended or adjusted under 35 U.S.C. 154(b) by 222 days.

(21) Appl. No.: 12/742,792

(22) PCT Filed: Nov. 11, 2008

(86) PCT No.: PCT/JP2008/070493
§ 371 (c)(1),
(2), (4) Date: Jun. 14, 2010

(87) PCT Pub. No.: WO2009/063858
PCT Pub. Date: May 22, 2009

(65) Prior Publication Data
US 2010/0246776 A1    Sep. 30, 2010

(30) Foreign Application Priority Data

Nov. 16, 2007   (JP) ............................... P2007-298026

(51) Int. Cl.
*H05G 1/64* (2006.01)
*A61B 6/14* (2006.01)

(52) U.S. Cl. ... 378/98.8; 378/189; 378/191; 250/370.09

(58) Field of Classification Search ................. 378/98.8, 378/189, 191; 250/370.09
See application file for complete search history.

(56) References Cited

U.S. PATENT DOCUMENTS

| | | | | |
|---|---|---|---|---|
| 5,331,166 A | * | 7/1994 | Yamamoto et al. | 250/370.11 |
| 5,434,418 A | * | 7/1995 | Schick | 250/370.11 |
| 5,691,539 A | * | 11/1997 | Pfeiffer | 250/370.09 |
| 6,030,119 A | * | 2/2000 | Tachibana et al. | 378/169 |
| 6,042,267 A | * | 3/2000 | Muraki et al. | 378/169 |
| 6,069,935 A | * | 5/2000 | Schick et al. | 378/98.8 |
| 6,201,249 B1 | * | 3/2001 | Yamayoshi | 250/370.11 |
| 6,307,915 B1 | * | 10/2001 | Frojdh | 378/98.8 |
| 6,320,934 B1 | * | 11/2001 | Carroll et al. | 378/98.8 |
| 6,404,854 B1 | * | 6/2002 | Carroll et al. | 378/98.8 |

(Continued)

FOREIGN PATENT DOCUMENTS

JP    07-280944    10/1995

(Continued)

*Primary Examiner* — Allen C. Ho
(74) *Attorney, Agent, or Firm* — Drinker Biddle & Reath LLP

(57) ABSTRACT

The present invention relates to an X-ray image acquiring apparatus having a structure for improving the quality of an image signal representing an X-ray image captured. The X-ray image acquiring apparatus (5) comprises an imaging section (7), a connecting section (8), and a signal cable (L1). The imaging section (7) outputs an image signal representing an X-ray image captured. The connecting section (8) has a structure attachable/detachable to a control circuit (6) for controlling the imaging section (7). The signal cable (L1) has one end connected to the imaging section (7) and the other end connected to the connecting section (8), and is flexible. The signal cable (L1) includes a detection signal line (L11), a control signal line (L12), an image signal line (L13), and a GND line (L14), which are used for transmitting signals exchanged between the imaging section (7) and the control circuit (6), and a shield member (5a) covering these lines (L11 to L14). The connecting section (8) includes a resistor (5c) provide between the shield member (5a) and a grounding terminal (81a) of the connecting section (8).

4 Claims, 4 Drawing Sheets

U.S. PATENT DOCUMENTS

| | | | | |
|---|---|---|---|---|
| 6,652,141 B1 * | 11/2003 | Cianciosi | | 378/191 |
| 6,924,486 B2 * | 8/2005 | Schick et al. | | 250/370.08 |
| 6,972,411 B2 * | 12/2005 | Schick et al. | | 250/370.11 |
| 7,015,478 B2 * | 3/2006 | Yamamoto | | 250/370.09 |
| 7,278,784 B2 * | 10/2007 | Hack et al. | | 378/191 |
| 7,538,327 B2 * | 5/2009 | Niwa | | 250/370.09 |
| 7,563,026 B2 * | 7/2009 | Mandelkern et al. | | 378/191 |
| 7,676,024 B2 * | 3/2010 | Taoka et al. | | 378/98.8 |
| 7,777,192 B2 * | 8/2010 | Ohta et al. | | 250/370.09 |
| 7,891,871 B2 * | 2/2011 | Ayraud | | 378/191 |
| 7,959,355 B2 * | 6/2011 | Stantchev | | 378/191 |
| 8,045,680 B2 * | 10/2011 | Taoka et al. | | 378/114 |

FOREIGN PATENT DOCUMENTS

| | | |
|---|---|---|
| JP | 10-074421 | 3/1998 |
| JP | 10-241471 | 9/1998 |
| JP | 2005-294511 | 10/2005 |
| JP | 2006-246962 | 9/2006 |

* cited by examiner (a)

(b)

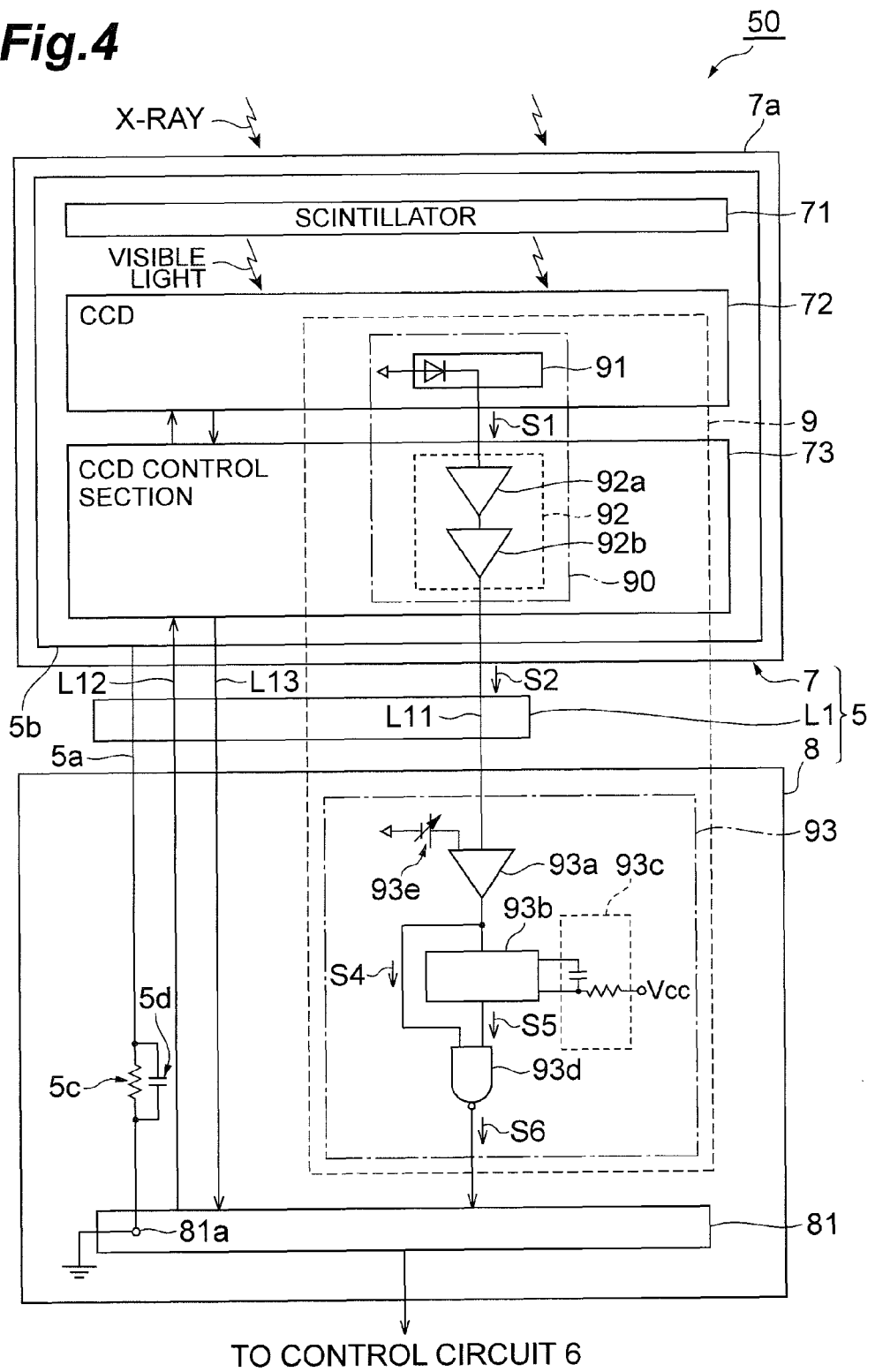

X-RAY IMAGE ACQUIRING APPARATUS

TECHNICAL FIELD

The present invention relates to an X-ray image acquiring apparatus including an X-ray image sensor (imaging section) which outputs a captured X-ray in age as an electric signal.

BACKGROUND ART

Patent Document 1 discloses an X-ray image sensor which outputs an X-ray image of an intraoral site or the like as an electric signal. This X-ray image sensor comprises an X-ray fluorescent screen, a CCD sensor, a container accommodating them, and the like. A conductive member such as an aluminum foil or the like surrounding the X-ray fluorescent screen, CCD sensor, and the like is disposed within the container and electrically grounded. The conductive member is connected to a shielding wire within a signal cable connected to the CCD sensor or the like.

Patent Document 1: Japanese Patent Application Laid-Open No. 7-280944

DISCLOSURE OF THE INVENTION

Problems that the Invention is to Solve

The present inventors have examined the conventional X-ray sensor, and as a result, have discovered the following problems. That is, the X-ray image sensor disclosed in Patent Document 1 is placed in various ways within a mouth. Therefore, the signal cable extending from the X-ray image sensor is routed and bent in various manners. In particular, the signal cable is bent very frequently at its junction with the X-ray image sensor. In the case that the signal cable is bent very frequently as such, the shielding wire may break. When the shielding wire breaks, a floating shield line in which a part of the shielding wire is in a floating state (electrically connected to nowhere) may be formed within the signal cable. The floating shield line may function as an antenna for noises, thereby collecting them. Depending on how the signal cable is bent, the floating shield line may come into and out of contact with the shielding wire, thereby letting noises enter the shielding wire or not. When a noise enters the shielding wire, the noise is superposed on an image signal transmitted through the signal cable from the CCD sensor, whereby the X-ray image sensor decreases its image quality.

The present invention has been developed to eliminate the problems described above. It is an object of the present invention to provide an X-ray image acquiring apparatus equipped with a structure for improving the quality of an image signal representing an X-ray image captured.

Means for Solving the Problems

The X-ray image acquiring apparatus according to the present invention comprises an imaging section, a connecting section, and a signal cable. The imaging section outputs an image signal representing an X-ray image captured. The connecting section has a structure attachable/detachable to a control circuit which controls the imaging section. The signal cable has one end connected to the imaging section and the other end connected to the connecting section. The signal cable is a flexible cable including a plurality of signal lines each of which transmits a signal exchanged between the imaging section and the control circuit.

In particular, in the X-ray image acquiring apparatus according to the present invention, the signal cable, which extends from the imaging section and has the connecting section attached to a leading end thereof, includes a shield member for covering the plurality of signal lines. This connecting section includes a resistance disposed between the shield member and a grounding terminal of the connecting section. Preferably, the resistance has a resistance value of 100 kΩ or more but 10 MΩ or less.

When the shield member breaks, a floating line in which a part of the shield member is in a floating state may be formed within the signal cable. The floating shield line may function as an antenna for noises, thereby collecting them. Depending on how the signal cable is bent, the floating shield line may come into and out of contact with the shielding member, thereby letting noises enter the shield member or not. In the X-ray image acquiring apparatus according to the present invention, however, the shield member within the signal cable is connected to the grounding terminal through the resistance. Therefore, even when a noise enters the shield member from the floating shield line, the noise flowing through the shield member is reduced by the resistance. Hence, the noise superposed on the image signal within the signal cable can be reduced.

The X-ray image acquiring apparatus according to the present invention may include a capacity disposed in parallel with the resistance between the shield member and the grounding terminal. Preferable, in this case, the resistance included in the connecting section has a resistance value of 100 kΩ or more but 10 kΩ or less, while the capacity has a capacity value of 10 pF or more but 1 μF or less.

Preferably, in the X-ray image acquiring apparatus according to the present invention, the resistance and capacity included in the connecting section are arranged in parallel with each other. In this case, even when noises enter the shield member from the floating shield line, those having high frequencies can be removed by flowing into the ground through the capacity, while those having other frequencies can be reduced by the resistance. Therefore, noises superposed on the image signal within the signal cable can sufficiently be reduced.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the scope of the invention will be apparent to those skilled in the art from this detailed description.

Effects of the Invention

As described above, the X-ray image acquiring apparatus according to the present invention can effectively reduce influences of noises caused by the state of installation of the signal cable and improve the quality of the image signal representing the captured X-ray image.

BRIEF DESCRIPTION OF THE DRAWINGS

FIG. 4 is a view showing the configuration of a second embodiment of the X-ray image acquiring apparatus according to the present invention.

DESCRIPTION OF THE REFERENCE NUMERALS

Figure 1:
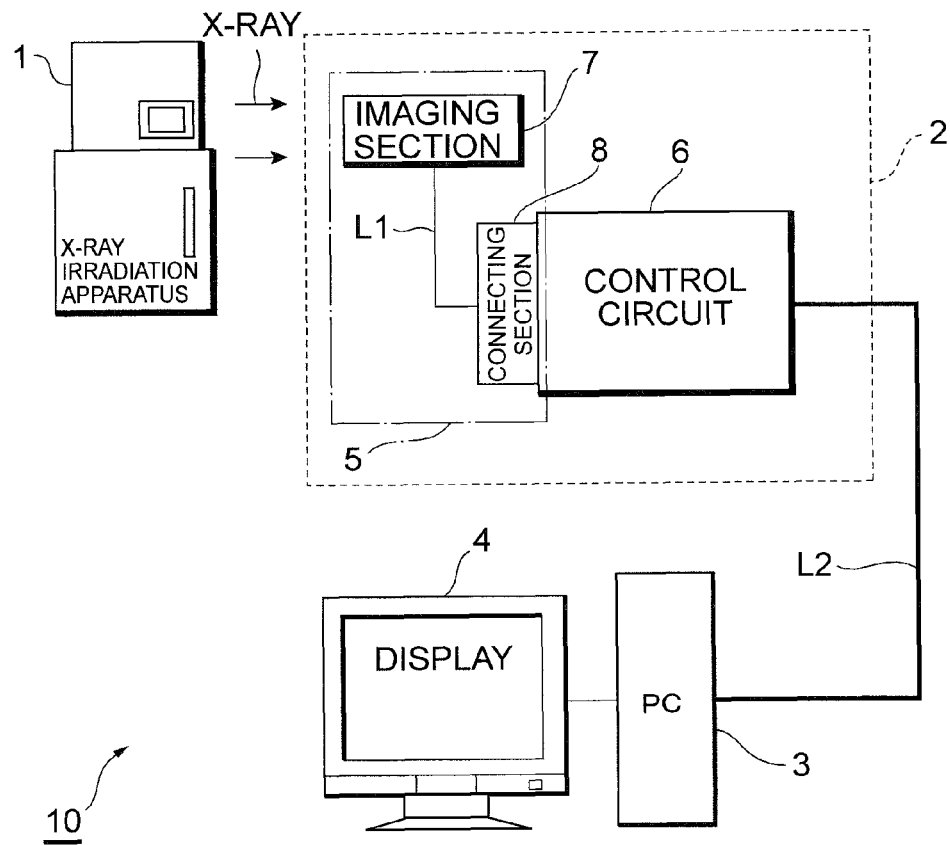
FIG. 1 is a view showing the configuration of an X-ray imaging system including the X-ray image acquiring apparatus according to the present invention.
Figure 1:
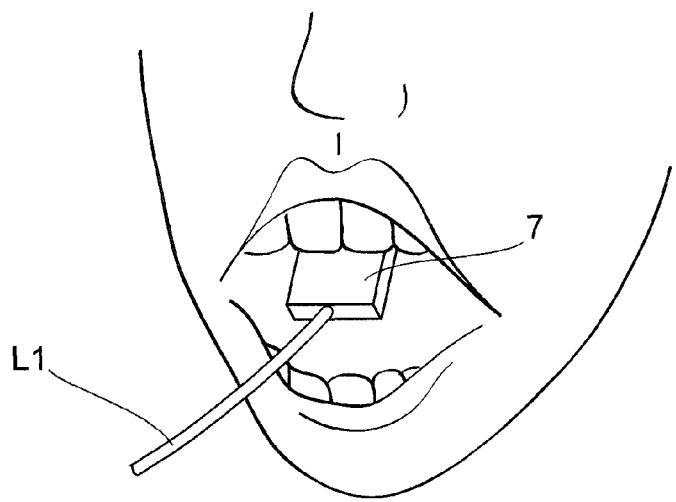

L1, L2 . . . signal cable; L11 . . . detection signal line; L12 . . . control signal line; L13 . . . image signal line; L14 . . . GND line; K1, K2, K3, K4 . . . cable; 1 . . . X-ray irradiation apparatus; 10 . . . X-ray imaging system; 11 . . . tube; 2 . . . X-ray imaging apparatus; 3 . . . PC; 4 . . . display; 5, 50 . . . X-ray image acquiring apparatus; 5a . . . shield member; 5c . . . resistor; 5d . . . capacitance; 5b . . . shield member; 6 . . . control circuit; 7 . . . imaging section; 7a . . . housing; 71 . . . scintillator; 72 . . . CCD; 73 . . . CCD control circuit; 8 . . . connecting section; 81 . . . connector; 81a . . . grounding terminal; 9 . . . trigger generating unit; 90 . . . X-ray detection circuit; 91 . . . PD; 92 . . . amplifier circuit; 92a . . . I-V conversion amplifier; 92b . . . gain amplifier; 93 . . . trigger generating circuit; 93a . . . comparator; 93c . . . RC circuit; 93d . . . NOR circuit; 93b . . . monostable multivibrator; and 93e . . . reference power supply.

BEST MODES FOR CARRYING OUT THE INVENTION

In the following, embodiments of the X-ray image acquiring apparatus according to the present invention will be explained in detail with reference to FIGS. 1 to 4. In the description of the drawings, identical or corresponding components are designated by the same reference numerals, and overlapping description is omitted.

FIG. 1 is a view showing the configuration of an X-ray imaging system including the X-ray image acquiring apparatus according to the present invention; in particular, the area (a) of FIG. 1 is a block diagram showing an X-ray imaging system 10, while the area (b) of FIG. 1 is a diagram for explaining an example of capturing an X-ray image. The X-ray imaging system 10 is a medical X-ray imaging system, which performs X-ray imaging for teeth of subjects and the like. As shown in the area (a) of FIG. 1, the X-ray imaging system 10 comprises an X-ray irradiation apparatus 1, an X-ray imaging apparatus (imaging section) 2, a PC 3 (PC: Personal Computer), and a display 4. The X-ray irradiation apparatus 1, which irradiates teeth and the like with X-rays, is of a permanent installation type.

In response to an input of an instruction to start X-ray irradiation, the X-ray irradiation apparatus 1 performs the X-ray irradiation until an instruction to terminate the X-ray irradiation is inputted (or a timer for terminating the irradiation expires). The X-ray irradiation apparatus 1 may be constructed such as to perform steady-state X-ray irradiation corresponding to a voltage waveform of a perfect DC voltage obtained corresponding to a half-wave rectified waveform of an AC power-supply voltage.

The X-ray imaging apparatus 2 is an apparatus for capturing an X-ray image of teeth and the like, and comprises an X-ray image apparatus 5 and a control circuit 6. The X-ray image acquiring apparatus 5 includes an imaging section 7 and a connecting section 8, while the imaging section 7 is connected to the connecting section 8 through a signal cable L1. The X-ray image acquiring apparatus 5 also has a trigger generating unit 9 which will be explained later. The imaging section 7 has a CCD 72 which will be explained later, while the CCD 72 captures an X-ray image of teeth and the like. The imaging section 7 has such a size and form as to be easily insertable into a mouth of a subject. The area (b) of FIG. 1 shows an example of states where the imaging section 7 is inserted into the mouth of the subject as an example of capturing an X-ray image. The imaging section 7 is inserted on the inside of front teeth on the upper jaw of the subject, while the signal cable L1 extends from the imaging section 7 to the outside of the mouth.

The control circuit 6 is connected to the PC 3 through a signal cable L2 such as a USB (Universal Serial Bus). In response to various control instructions transmitted from the PC 3 to the X-ray image acquiring apparatus 5, the control circuit 6 controls the X-ray image acquiring apparatus 5 (the imaging section 7 in particular), transmits image data to the PC 3, and so forth.

Through the signal cable L2, the PC 3 provides various settings for the X-ray imaging apparatus 2, instructs the latter on X-ray imaging, fetches image data indicative of the X-ray image from the X-ray imaging apparatus 2, so as to perform various analyses (e.g., extraction and expansion of specific regions in the image), stores the image data and data representing results of the analyses into a memory, and so forth. In accordance with the image data fetched from the X-ray imaging apparatus 2, the PC 3 causes the display 4 to show the X-ray image, the above-mentioned results of analyses of the image data, and the like. The display 4 encompasses display devices such as CRT (Cathode Ray Tube) and LCD (Liquid Crystal Display).

Figure 2:
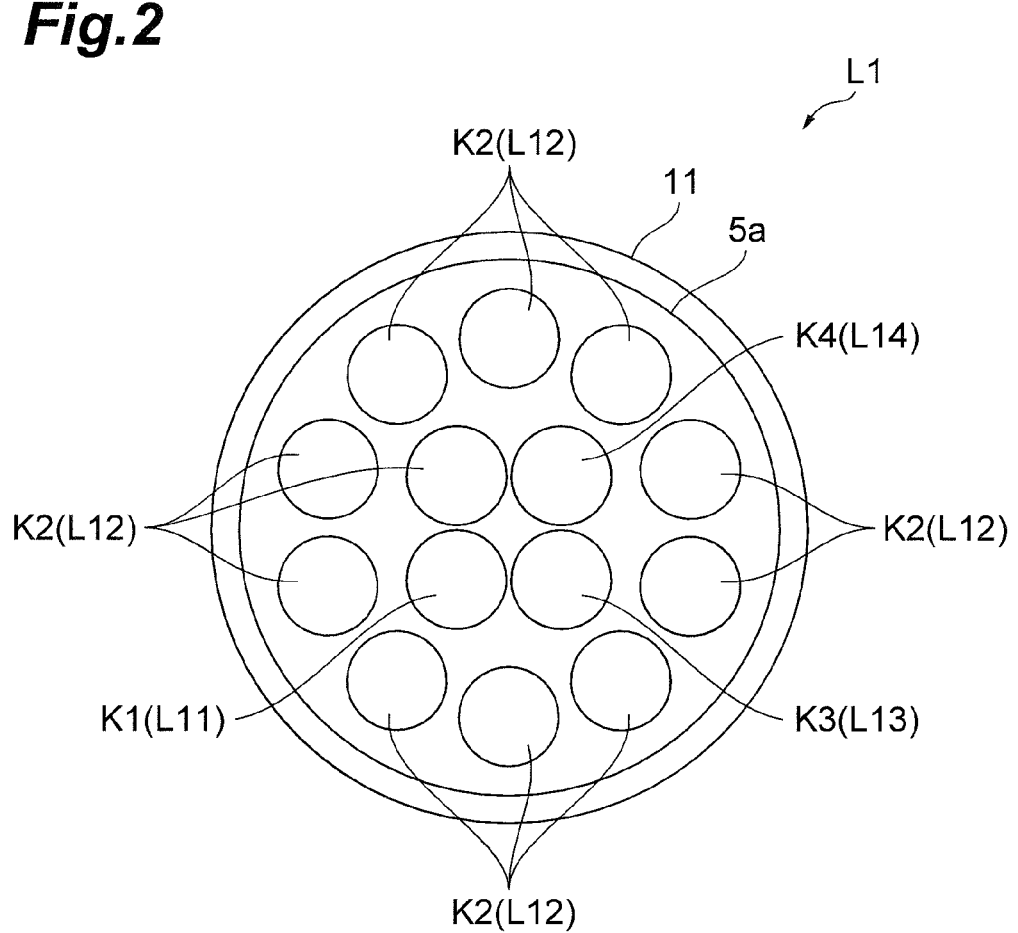
FIG. 2 is a view showing a cross-sectional structure of a signal cable shown in FIG. 1.

FIG. 2 is a view showing a cross-sectional structure of the signal cable L1. The signal cable L1 is a multicore cable comprising a tube 11 and ten-odd (fourteen cables in the embodiment shown in FIG. 2) cables K1 to K4 bundled within the tube 11. The signal cable L1 has an elongated form with a length of about 2 m and a diameter of about 3 mm. The tube 11 is composed of a material (e.g., PVC or fluororesin) excellent in flexibility such as to reduce discomfort and pains of the subject in the state where the imaging section 7 is inserted within the mouth of the subject (see the area (b) of FIG. 1).

Figure 3:
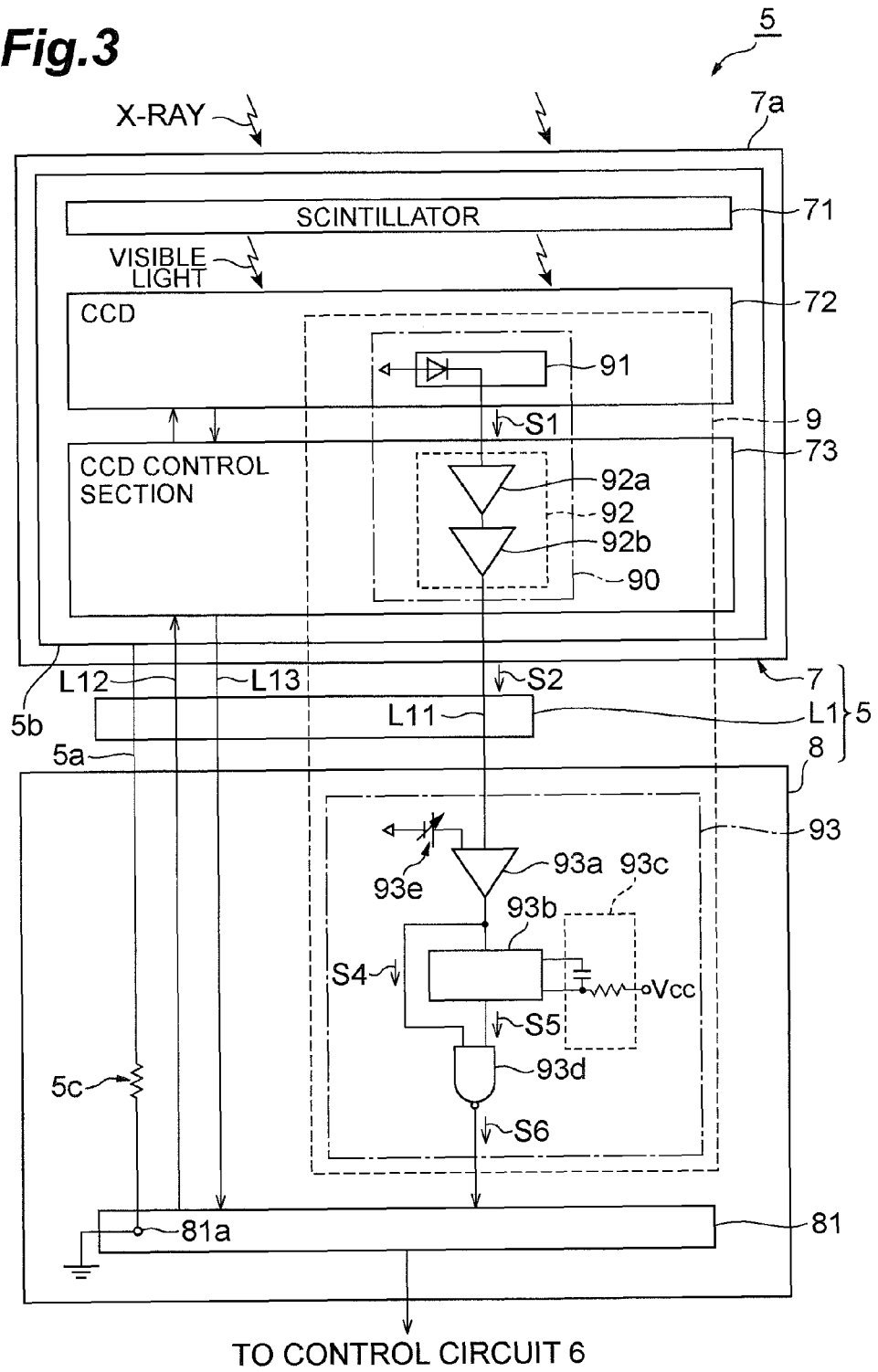
FIG. 3 is a view showing the configuration of a first embodiment of the X-ray image acquiring apparatus according to the present invention.

The signal cable L1 includes one cable K1, one cable K3, one cable K4, and eleven cables K2. The cable K1, the cable K3, the cable K4, and one of the cables K2 are placed in the center part of the signal cable L1 and surrounded by the ten cables K2 arranged on the periphery of these four cables. The cables K1 to K4 correspond to a detection signal line L11, a control signal line L12, an image signal line L13, and a GND line L14 (GND: Ground) which are shown in FIG. 3, respectively. FIG. 3 is a view showing the configuration of the first embodiment of the X-ray image acquiring apparatus according to the present invention.

The signal cable L1 includes a shield member 5a. The shield member 5a is disposed on the inside of the tube 11 and covers the cables K1 to K4. The shield member 5a is made of a conductive material and has flexibility. The shield member 5a shields the inside of the signal cable L1 (the inside of the tube 11) from the outside thereof. The shield member 5a is connected to a shield member 5b disposed within a housing 7a of the imaging section 7 shown in FIG. 3, so as to be electrically connected through a resistor 5c to a grounding terminal 81a of a connector 81 (having a structure attachable/detachable to the control circuit 6) of the connecting section 8. The resistor 5c constructs a low-pass filter together with a floating capacity formed by the shield member 5a. The resistor 5c has a resistance value of 100 kΩ or more but 10 MΩ or less.

In FIG. 3, the imaging section 7 comprises a scintillator 71, a CCD 72, and a CCD control circuit 73, which are accommodated within the housing 7a. The scintillator 71 emits visible light by a quantity corresponding to the amount of energy of an X-ray incident thereon. When irradiated with the visible light from the scintillator 71, the CCD 72 photoelectrically converts the visible light into an electric charge (an electric charge representing the image, which will hereinafter be referred to as image information) corresponding to the quantity of the visible light and accumulates the electric charge in a readable state (which means imaging).

The CCD control circuit 73 is connected to the CCD 72, control signal line L12, and image signal line L13. Upon receiving a control signal for the CCD 72 from the control circuit 6 through the control signal line L12, the CCD control circuit 73 controls driving of the CCD 72 according to the control signal. Examples of the control signal for the CCD 72 include instructions to capture the X-ray image and read the image information indicative of the X-ray image. According to the control by the control circuit 6, the CCD control circuit 73 reads the image information from the CCD 72 and outputs thus read image information to the control circuit 6 through the image signal line L13.

The conductive shield member 5b is disposed within the housing 7a and covers the CCD 72, the CCD control circuit 73, and the like. The shield member 5b electrically shields the inside of the imaging section 7 (the inside of the housing 7a) from the outside. The shield member 5b is connected to the shield member 5a within the signal cable L1.

The connecting section 8 is attached to one end of the signal cable L1 and functions to detachable connect the X-ray image acquiring apparatus 5 to the control circuit 6 (by an electric connection through the signal cable L1). The control signal for the imaging section 7 is transmitted from the control circuit 6 to the imaging section 7 through the connecting section 8 and control signal line L12. The image information read from the CCD 72 is transmitted to the control circuit 6 through the image signal line L13 and connecting section 8.

The connecting section 8 has the connector 81 and resistor 5c. The connector 81 has the grounding terminal 81a. The resistor 5c is disposed between and connected to the shield member 5a and grounding terminal 81a. The grounding terminal 81a is electrically connected to the shield member 5a through the resistor 5c.

The trigger generating unit 9 will now be explained. The trigger generating unit 9 generates a trigger signal which indicates when to start and end capturing the X-ray image, and outputs the trigger signal to the control circuit 6. The trigger generating unit 9 has an X-ray detection circuit 90, the detection signal line L11, and a trigger generating circuit 93. The X-ray detection circuit 90 has a PD 91 (PD: Photo Diode) and an amplifier circuit 92. The X-ray detection circuit 90 is provided in the imaging section 7.

The PD 91 is a monitoring photodiode for monitoring the X-ray irradiating the imaging section 7, and is provided in the CCD 72. The PD 91 is connected to the amplifier circuit 92. The PD 91 detects the visible light generated by the X-ray emitted from the X-ray irradiation apparatus 1. The PD 91 outputs an electric signal (hereinafter referred to as signal S1) corresponding to the amount of energy of the detected X-ray. The signal S1 includes a pulse P1 having a pulse width corresponding to the X-ray irradiation period (several tens of milliseconds to several seconds).

The amplifier circuit 92 is provided in the CCD control circuit 73. The amplifier circuit 92 has an I-V conversion amplifier 92a and a gain amplifier 92b. The I-V conversion amplifier 92a is connected to the PD 91 and gain amplifier 92b, while the gain amplifier 92b is connected to the I-V conversion amplifier 92a and the detection signal line L11. The I-V conversion amplifier 92a converts the signal S1 fed from the PD 91 from a current value to a voltage value, while the gain amplifier 92b amplifies the signal S1 converted to the voltage value to a signal level which can be processed by the trigger generating circuit 93 in a later stage, so as to generate a signal S2 (X-ray detection signal). The gain amplifier 92b outputs this signal S2 to the trigger generating circuit 93 through the detection signal line L11.

The trigger generating circuit 93 has a comparator 93a, a monostable multivibrator 93b, an RC circuit 93c, and a NOR circuit 93d. The trigger generating circuit 93 is provided in the connecting section 8. The trigger generating circuit 93 is connected to the X-ray detection circuit 90 through the detection signal line L11. The comparator 93a is connected to the detection signal line L11, a reference power supply 93e, the monostable multivibrator 93b, and the NOR circuit 93d, and further to the gain amplifier 92b through the detection signal line L11. When the signal S2 fed through the detection signal line L11 is at a reference signal level S3 or higher, the comparator 93a outputs a signal S4 to the monostable multivibrator 93b and NOR circuit 93d. The reference signal level S3 is determined by the reference power supply 93e that is variable. The signal S4 includes a pulse P2 having a pulse width corresponding to a time width in which the signal S2 is at the reference level S3 or higher (the time width substantially identical to the X-ray irradiation period).

The monostable multivibrator 93b is connected to the comparator 93a and NOR circuit 93d, while the RC circuit 93c is connected to the monostable multivibrator 93b and a DC power supply Vcc. When fed with the signal S4 from the comparator 93a, the monostable multivibrator 93b outputs a pulse P3 (signal S5) to the NOR circuit 93d in synchronization with the leading edge (start) of the pulse P2 contained in the signal S4. The pulse P3 has a pulse width (20 to 40 msec) determined by the respective values of the capacitance C and resistance R included in the RC circuit 93c.

The NOR circuit 93d is connected to the comparator 93a and monostable multivibrator 93b. When the signal S5 includes the pulse P3 or the signal S4 includes the pulse P2, the NOR circuit 93d keeps outputting a Low signal over a period during which this state continues. Otherwise, i.e., when the signal S5 does not include the pulse P3 and the signal S4 does not include the pulse P2, the NOR circuit 93d keeps outputting a High signal over a period during which this state continues. Therefore, during the X-ray irradiation period, the NOR circuit 93d outputs a trigger signal S6 including the Low signal pulse P4 having a pulse width corresponding to the length of this period (a trigger signal indicating when to start and end capturing the X-ray image). The trigger generating unit 9 can output the trigger signal S6 indicative of when to start and end capturing the X-ray image for any of the steady-state X-ray irradiation corresponding to a voltage waveform of a perfect DC voltage obtained by a high-frequency inverter scheme and the periodic X-ray irradiation corresponding to a half-wave rectified waveform of an AC power-supply voltage.

When the shield member 5a breaks in the X-ray image acquiring apparatus 5 according to the first embodiment, this breakage may yield a floating shield line in which a part of the shield member is in a floating state within the signal cable L1. The floating shield line may function as an antenna for noises, thereby collecting them. Depending on how the signal cable L1 is bent, the floating shield line may come into and out of contact with the shield member 5a, thereby letting noises enter the shield member or not. Since the shield member 5a within the signal cable L1 is connected to the grounding terminal 81a through the resistor 5c, however, even when a noise enters the shield member 5a from the floating shield line, the noise flowing through the shield member 5a is reduced by the resistor 5c. Hence, the noise superposed on the image signal within the signal cable L1 can be reduced.

FIG. 4 is a view showing the second embodiment of the X-ray image acquiring apparatus according to the present invention. The X-ray image acquiring apparatus 50 according to the second embodiment further comprises a capacitor 5d having a capacitance value of 10 pF or more but 1 µF or less in addition to the structure of the X-ray image acquiring apparatus 5 according to the first embodiment. It differs from the X-ray image acquiring apparatus 5 according to the first embodiment only in this point. The capacitor 5d is disposed in parallel with the resistor 5c between the shield member 5a and grounding terminal 81a. That is, the shield member 5a within the signal cable L1 is connected to the grounding terminal 81a through the resistor 5c and capacitor 5d. Therefore, even when noises enter the shield member 5a from the floating shield line, those having high frequencies can be removed by flowing into the ground through the capacitor 5d, while those having other frequencies are reduced by the resistor 5c. Hence, noises superposed on the image signal within the signal cable L1 can sufficiently be reduced.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

INDUSTRIAL APPLICABILITY

The X-ray image acquiring apparatus according to the present invention is applicable to X-ray imaging systems which are widely utilized in technical fields of medical care, electronic devices, and the like.

The invention claimed is:

1. An X-ray image acquiring apparatus, comprising:
   an imaging section capturing an X-ray image and outputting an image signal representing the X-ray image;
   a connecting section having a structure attachable/detachable to a control circuit which outputs a control signal for controlling the imaging section; and
   a signal cable having one end connected to the imaging section and the other end connected to the connecting section, the signal cable including a plurality of signal lines each of which transmits a signal exchanged between the imaging section and the control circuit, and having flexibility,
   wherein the signal cable includes a shield member covering the plurality of signal lines, and
   wherein the connecting section includes a resistor provided between the shield member and a grounding terminal of the connecting section.

2. An X-ray image acquiring apparatus according to claim 1, further comprising a capacitor provided in parallel with the resistor between the shield member and the grounding terminal.

3. An X-ray image acquiring apparatus according to claim 2, wherein the resistor has a resistance value of 100 kΩ or more but 10 MΩ or less, and
   wherein the capacitor has a capacitance value of 10 pF or more but 1 µF or less.

4. An X-ray image acquiring apparatus according to claim 1, wherein the resistor has a resistance value of 100 kΩ or more but 10 MΩ or less.

* * * * *